United States Patent
Otomo et al.

(10) Patent No.: US 6,423,739 B1
(45) Date of Patent: Jul. 23, 2002

(54) METHOD FOR AIDING CEREBRAL RECOVERY FOLLOWING NEURODEGENERATION

(75) Inventors: Eiichi Otomo; Yoshiyuki Takasu, both of Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/784,048

(22) Filed: Feb. 16, 2001

Related U.S. Application Data

(63) Continuation-in-part of application No. 09/511,952, filed on Feb. 23, 2000, now abandoned.

(51) Int. Cl.$^7$ ............................................. A61K 31/40
(52) U.S. Cl. ...................................... 514/424
(58) Field of Search ........................................ 514/424

(56) References Cited

U.S. PATENT DOCUMENTS

| | | | |
|---|---|---|---|
| 4,341,790 A | 7/1982 | Betzing et al. | ............. 424/274 |
| 5,886,023 A | 3/1999 | Otomo et al. | ............... 514/424 |
| 6,107,330 A | 8/2000 | Nabeshima et al. | ......... 514/424 |
| 6,281,242 B1 | 8/2001 | Regan et al. | ............... 514/424 |

FOREIGN PATENT DOCUMENTS

| | | |
|---|---|---|
| DE | 29 23 975 A1 | 12/1980 |
| DE | 29 24 011 A1 | 12/1980 |
| EP | 0 515 866 A1 | 12/1992 |
| EP | 1 020 189 A1 | 7/2000 |
| EP | 1 022029 A1 | 7/2000 |
| WO | 96/02207 A1 | 2/1997 |
| WO | 97/03485 A1 | 4/1998 |
| WO | 98/03162 A1 | 1/1999 |
| WO | 98/04136 A1 | 3/1999 |
| WO | 99/04264 A1 | 2/2000 |
| WO | 00/03484 A1 | 12/2000 |

OTHER PUBLICATIONS

Effects of the new cognition–enhancing agent nefiracetam in rats with cerebral embolism. Arzneimittel–Forschung, (1992 Nov.) 42 (11) 1274–8.
Nefiracetam, a novel cognition–enhancing agent, An introductory overview. Arzneimittel–Forschung, (1994 Feb.) 44 (2A) 193–4.
Improvement of impaired brain monoamine metabolism by the cognition–enhancing agent nefiracetam after microsphere–induced cerebral embolsim in rats. Arzneimittel–Forschung, (1994 Feb.) 44 (2A) 195–8.
General pharmacological profile of the new cognition–enhancing agent nefiracetam. Arzneimittel–Forschung, (1994 Feb.) 44 (2A) 199–210.
Nefiracetam prevents propofol–induced anterograde and retrograde amnesia in the rodent without compromising quality of anesthesia. Anesthesiology, (1998 Sep.) 89 (3) 699–706.
Influence of nefiracetam on NGF–induced neuritogenesis and neural adhesion molecule polysialic acid expression in vivo and in vitro comparisons. Behavioural Brain Research, (1997 Feb.) 83 (1–2) 173–8.
Effects of the subacute administration of nefiracetam on abnormal behavior in aged rats. Behavioural Brain Research, (1996 Aug.) 78 (2) 93–100.
Effects of nefiracetam on amnesia animal models with neuronal dysfunctions. Behavioural Brain Research, (1997 Feb.) 83 (1–2) 107–15.
Cellular mechanisms underlying cognition–enhancing actions of nefiracetam (DM–0384). Behaviorual Brain Research, (1997 Feb.) 83 (1–2) 185–8.
Nefiracetam ameliorates learning deficits in older rabbits and may act via the hippocampus. Behaviorual Brain Research, (1997 Feb.) 83 (1–2) 179–84.
Effects of nefiracetam on deficits in active avoidance response and hippocampal cholinergic and monoaminergic dysfunctions induced by AF64A in mice. Journal of Neural Transmission. General Section, (1994) 95 (3) 179–93.
Nefiracetam enhances acetylcholine outflow from the frontal cortex: in vivo microdialysis study in the rat. Journal of Neural Transmission. General Section, (1994) 98 (1) 15–22.
Effects of nefiracetam, a novel pyrrolidone derivative, on brain monoamine metabolisms in mice. Journal of Neural Transmission. General Section, (1992) 90(2) 125–36.
Effects of nefiracetam, DM–9384 on amnesia and decrease in cholineacetyltransferase activity induced by cycloheximide. Journal of Neural Transmission. General Section, (1992) 90 (2) 103–11.
Nefiracetam (DM–9384) reverses apomorphine–induced amnesia of a passive avoidance response: delayed emergence of the memory retention effects. Neurochemical Research, (1996 Jun.) 21 (6) 649–52.
Effects of the nootropic drug nefiracetam on the GABA$_A$ receptor–channel complex in dorsal root ganglion neurons. Neuropharmacology, (1996) 35 (9–10) 1251–61.
Electric field distribution of event–related potentials in stroke patients. Brain Topography, (1996 Spring) 8 (3) 279–84.
Apomorphine–induced hypoattention in rats and reversal of the choice performance impairment by aniracetam. European Journal of Pharmacology,(Jan. 26, 1998) 342 (2–3) 127–38.
Nefiracetam (DM–9384): effect on eyeblink classical conditioning in older rabbits. Psychopharmacology, (1994 Mar.) 114 (2) 200–8.
Mecamylamine–or scopolamine–induced learning impairment: ameliorated by nefiracetam. Psychopharmacology, (1997 May) 131 (2) 130–9.

(List continued on next page.)

*Primary Examiner*—Phyllis G. Spivack
(74) *Attorney, Agent, or Firm*—Sughrue Mion, PLLC

(57) ABSTRACT

A method for aiding cerebral recovery following neurodegeneration, particularly after a stroke, in a mammal, by administration of nefiracetam is disclosed. This method of treatment allows an improvement in the recovery from stroke.

16 Claims, No Drawings-

OTHER PUBLICATIONS

A 'long–term–potentiation–like' faciliation of hippocampal synaptic transmission induced by the nootropic nefiracetam. Brain Research, (May 1, 1999) 826 (2) 281–8.

Modulation of the neuronal nicotinic acetylcholine receptor–channel by the nootropic drug nefiracetam. Brain Research, (Mar. 20, 1999) 822 (1–2) 72–9.

Hippocampus in delay eyeblink classical conditioning: essential for nefiracetam amelioration of learning in older rabbits. Brain Research 747, (1997) 207–218.

Enhancement of neuronal calcium channel currents by the nootropic agent, nefiracetam (DM–9384), in NG108–15 cells, Brain Research 642 (1994) 123–131.

Piracetam and other structurally related nootropics. Brain Research. Brain Research Reviews, (1994 May) 19 (2) 180–222.

Effects of nefiracetam (DM–9384), a pyrrolidone derivative, on brain monoamine systems. Archives Internationals de Pharmacodynamie et de Therapie, (1994 Sep.–Oct) 328 (2) 125–44.

Single–and multiple–dose pharmacokinetics of Nfiracetam, a new nootropic agent, in healthy volunteers. Journal: J Pharm Pharmacol, 44 (9) 750–4 1992.

Possible involvement of the activation of voltage–sensitive calcium channels in the ameliorating effects of nefiracetam on scopolamine–induced impairment of performance in a passive avoidance task. Journal of Pharmacology and Experimental Therapeutics, (1994 Sep.) 270 (3) 881–92.

Nefiracetam elevates extracellular acetylcholine level in the frontal cortex of rats with cerebral cholinergic dysfuntions: an in vivo microdialysis study. Neuroscience Letters, (Apr. 24, 1998) 246 (2) 69–72.

Effects of nefiracetam on drug–induced impairment of latent learning in mice in a water finding task. European Journal of Pharmacology, (Apr. 1, 1994) 255 (1–3) 57–65.

Involvement of the cholinergic system in the effects of nefiracetam (DM–9384) on carbon monoxide (CO)–induced acute and delayed amnesia. European Journal of Pharmacology, (Jun. 5, 1992) 216 (2) 279–85.

Improvement by nefiracetam of β–amyloid–(1–42)–induced learning and memory impairments in rats. British Journal of Pharmacology, (1999 Jan.) 126 (1) 235–44.

Facilitatory actions of the cognitive enhancer nefiracetam on neuronal Ca2+channels and nicotine ACh receptors: their intracellular signal transduction pathways. Nippon Yakurigaku Zasshi. Folia Pharmacologica Japonica, (1998 Oct.) 112 Suppl 1 41P–43P.

Nefiracetam modulates acetylcholine receptor currents via two different signal transduction pathways. Molecular Pharmacology, (1998 Jan.) 53 (1) 1–5.

A therapeutic strategy to prevent morphine dependence and tolerance by coadministration of cAMP–related reagents with morphine. Methods and Findings in Experimental and Clinical Pharmacology, (1998 Sep.) 20 (7) 619–25.

DM–9384, a new cognition–enhancing agent, increases the turnover of components of the GABAergic system in the rat cerebral cortex. European Journal of Pharmacology, (Jul. 20, 1993) 238 (2–3) 303–9.

Nefiracetam (DM–9384) preserves hippocampal neural cell adhesion molecule–mediated memory consolidation processes during scopolamine disruption of passive avoidance training in the rat. Journal of Neurochemistry, (1993 Jul.) 61 (1) 266–72.

Effects of DM–9384, a pyrrolidone derivative, on ischemia–induced changes in the central monoamine systems. Pharmacology,Biochemistry and Behavior, (1992 Jan.) 41 (1) 231–4.

Reversal effect of DM–9384 on scopolamine–induced acetylcholine depletion in certain regions of the mouse brain. Psychopharmacology, (1991) 105 (3) 310–6.

Effects of DM–9384, a cyclic derivative of GABA, on amnesia and decreases in $GABA_A$ and muscarinic receptors induced by cycloheximide. Journal of Pharmacology and Experimental Therapeutics, (Apr. 1991) 257 (1) 271–5.

Effects of DM–9384, a pyrrolidone derivative, on alcohol––and chlordiacepoxide–induced amnesia in mice. Pharmacology,Biochemistry and Behavior, (1990 Jun.) 36 (2) 233–6.

Effects of DM–9384 in a model of amnesia based on animals with GABAergic neuronal dysfunctions. European Journal of Pharmacology, (Mar. 20, 1990) 178 (2) 143–9.

Protective effect of DM–9384, a novel pyrrolidone derivative, against experimental cerebral anoxia. Japanese Journal of Pharmacology, (1990 Sep.) 54 (1) 33–43.

Effects of N–(2, 6–dimethylphenyl)–2–(2–oxo–1–pyrrolidinyl)acetamide ( DM–9384) on learning and memory in rats. Japanese Journal of Pharmacology, (1989 May) 50 (1) 47–53.

Effects of DM–9384 and Aniracetam on Learning in Normal and Basal Forebrain–Lesioned Rats. Res Commun Psychol Psychiatry Behav, (1991) 16 (1–2), 1–14.

Nefiracetam. CNS Drugs, (1996) 6/4 (331–337).

Arisugacins, selective acetylcholinesterase inhibitors of microbial origin. Pharmacology and Therapeutics, (1997) 76/1–3 (45–54).

Nefiracetam [1]. CNS Drugs, (1996) 6/4 (338). (Woodruff––Pak).

Nefiracetam viewpoint. CNS Drugs, (1996) 6/4 (338). (Nabeshima).

The medicinal chemistry of Alzheimer's and Alzheimer–like diseases with emphasis on the cholinergic hypothesis. Farmaco, (1995) 50/7–8 (489–503).

Quantitative effects of nefiracetam on spatial learning of rats with cerebral embolism. Stroke, (Jan. 1999) vol. 30, No. 1, pp. P88–P88.

Le, et al, Quantitative Effects of Nefiracetam on Spatial Learning of Rats After Cerebral Embolism; Journal of Stroke and Cerebrovascular Diseases, vol. 10, No. 3 (May–Jun.), 2001: pp 99–105.

METHOD FOR AIDING CEREBRAL RECOVERY FOLLOWING NEURODEGENERATION

CROSS REFERENCE TO RELATED APPLICATIONS

This is a continuation-in-part of application Ser. No. 09/511,952, filed on Feb. 23, 2000 abandoned.

FIELD OF THE INVENTION

The present invention concerns the use of a cyclic gamma-aminobutyric acid (GABA) derivative, namely N-(2,6-dimethylphenyl)-2-(2-oxo-1-pyrrolidinyl) acetamide, as a drug for combating neurodegeneration, particularly after a stroke, for improving the Activities of Daily Living (ADL) after a stroke or for recovering, or at least for improving the recovery of, a post-stroke patient.

BACKGROUND OF THE INVENTION

It is known that a way to assess physical impairment in post-stroke patients, besides the neurological motor and sensory examination, is to quantitate deficits in the performance of daily activity (ADL) according to assessment scales, such as the John Hopkins Functioning Inventory (JHFI) or analogous ones, which determine the patients' ability to accomplish normal operations, in particular keeping the sitting or standing position, walking, washing, dressing, undressing, eating meals, bathing and using the lavatory. The assessment, the impairment, as well as and the need of recovery of ADL after stroke are illustrated by Robert G. Robinson "The Clinical Neuropsychiatry of Stroke", 1998, Cambridge University Press, pages 143, 222–225 and 292–293.

Depression is the main disorder associated with stroke and there is a correlation between the severity of depression and the severity of impairment in ADL. For the improvement in the impairment of ADL and, as a consequence, for the improvement in the recovery from stroke, patients are mainly treated with antidepressant drugs and, according to the above cited reference, there are no documented pharmacological treatments, apart from said antidepressants treatments, which improve physical or cognitive recovery from completed stroke. Supra Robinson, p. 293.

Cyclic GABA derivatives, more particularly 2-oxopyrrolidine derivatives, are compounds extensively used in pharmaceutical compositions for the improvement of memory and attention and are known as mnemotonic or nootropic agents. Typical drugs of this class include 2-oxo-1-pyrrolidineacetamide (piracetam), 1-(4-methoxybenzoyl)-2-pyrrolidinone (aniracetam) and 4-hydroxy-2-oxo-1-pyrrolidineacetamide (oxiracetam).

DESCRIPTION OF THE ART

It is known (BE 883791-U.S. Pat. No. 4,341,790) that anilides of 2-oxo-1-pyrrolidineacetamide show central vasoactive and tranquilizing properties as well as the ability of regulating the metabolism and inhibiting thrombocyte agglutination. Thus, said compounds are deemed to be useful for the treatment of cerebro-ischaemic or atrophic diseases, brain irrigation disorders, brain atrophic crises as well as of brain aging processes. Among these anilides of 2-oxo-1-pyrrolidineacetamide, the 2,6-dimethylanilide, i.e., N-(2,6-dimethylphenyl)-2-(2-oxo-1-pyrrolidinyl)acetamide, known and hereinafter referred to as nefiracetam, represented by the formula (A)

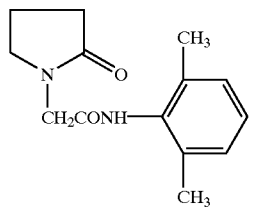

has been reported to be effective in prolonging the survival time upon a decrease in blood oxygen level and in relieving failure of memory due to cerebropathy.

The literature extensively discloses (see for example E. Ohtomo et al., J Clin. Exp. Med., Suppl., 1994, 170/9, 777–816) the usefulness of nefiracetam in improving psychiatric disorders associated with cerebrovascular diseases such as stroke (cerebral infarction or cerebral hemorrhage), this activity being a consequence of the favorable action of nefiracetam on the cerebral irrigation, as suggested by BE 883791.

It is also known (K. Hirata et al., Brain Topography 1996, 8/3, 279–284) that nefiracetam acts as a cerebral metabolic enhancer in improving the mental function impairment in stroke patients, thus confirming the suggestion of BE 833791 which disclosed the metabolism-regulating properties of the compound. Hirata et al., however, conclude that the improvement of mental function tests was not significant.

Moreover, it is known (U.S. Pat. No. 5,886,023) that nefiracetam improves symptoms of cerebrovascular or Alzheimer's type dementia due to a decline in mental function.

All these documents indicate that the efficacy of nefiracetam in the symptomatic treatment of impaired mental function is due to its ability in improving the cerebral irrigation or to its metabolism-regulating properties. Psychiatric symptoms and cognitive impairment are frequently observed following stroke and negatively affect both the patient and the caregiver.

In the above-cited article of Ohtomo et al., the global results of a clinical study, conducted in two groups of patients to which nefiracetam and, respectively, placebo were administered after a stroke (cerebral infarction or celebral hemorrhage), showed that the compound improves the psychiatric symptoms but concluded that there was no significant difference between the two groups as far as the activities of daily living were concerned. Thus, according to these results nefiracetam appeared as inactive in improving the disturbances of the activities of daily living in post-stroke patients. A positive effect in this indication could suggest a curative use of a drug for the recovery from a stroke or, at least, for an improved recovery from stroke.

SUMMARY OF THE INVENTION

It has now surprisingly been found that, if nefiracetam is administered to a patient, suffering from the consequences of a stroke, early after the event or at the most within the first six months after the stroke, a significant improvement with regard to the global disturbances of the activities of the daily living is observed.

More particularly, it has been found that nefiracetam is able to induce an improvement in the recovery of post-stroke patients, provided that said nefiracetam is administered early after the event, at the most within the first six months after said event.

Moreover, it has surprisingly been found that nefiracetam possesses a remarkable neurotrophic activity which allows the regeneration of damaged neurons, thus being able to combat neurodegeneration, and that nefiracetam is particularly effective when the neurodegeneration is due to a stroke (cerebral infarction or cerebral hemorrhage).

The mechanism by which nefiracetam acts on the neurodegeneration, thus allowing, for example, a recovery or at least an improvement in the recovery from stroke, is unknown because nefiracetam does not possess known biochemical activities which are predictive and known for this action such as, for example an agonism for the 5HT1-A receptor or a positive modulation of AMPA-sensitive glutamate receptors (AMPA indicates $\alpha$-amino-3-hydroxy-5-methyl-4-isoxazolepropionic acid).

The neurotrophic, in particular anti-neurodegenerative property of nefiracetam, which was inferred on the basis of the clinical evidence of a significant improvement in the Activities of the Daily Living was confirmed by biochemical and animal tests.

DETAILED DESCRIPTION OF THE INVENTION

Thus, it is an object of the present invention to provide a method for improving the Activities of Daily Living (ADL) in a post-stroke patient which comprises administering to said patient an effective dose of nefiracetam, said administration being initiated within the first six months after the event.

In order to display the best activity, nefiracetam will be administered early or at least as soon as possible, advantageously within three month, preferably within one month after the stroke.

Nefiracetam can be administered in various manner to achieve the desired effect, for example for improving ADL in a post stroke patient or for the recovery of, or at least for improving the recovery of, a post-stroke patient. The compound can be administered alone or in the form of pharmaceutical compositions comprising a pharmacologically effective amount of nefiracetam as an active ingredient and a pharmaceutical acceptable carrier to the patient to be treated, preferably orally. The oral amount of nefiracetam administered will vary and can be any effective amount according to the physician's prescription. Normally, depending upon the patient and the mode of administration, the quantity of compound administered orally may vary over a wide range to provide from about 1 mg/kg to about 20 mg/kg, usually 1.5 mg/kg to 15 mg/kg of body weight of the patient per dose. Unit doses of nefiracetam in the oral pharmaceutical compositions may contain, for example, from about 50 mg to about 1200 mg, usually from 100 to 600 mg of the compound and may be administered 1 to 4 times daily.

The activity of nefiracetam to improve ADL in post-stroke patients has been discovered during a controlled clinical trial against placebo. The compound has been administered orally to 32 post-stroke patients within six months after the event whilst, concurrently, 27 patients received placebo. The two groups of patients were followed during at least 8 weeks and followed up at the end of week 4 and at the end of week 8 on a symptom scale measuring Activities of Daily Living. The nefiracetam-treated patients showed a moderate or remarkable improvement, whereas no patient in the group treated with placebo showed an improvement. Among the above 59 patients, 19 received nefiracetam and 10 received placebo within three months after stroke. Some 70% of the nefiracetam-treated patients showed a moderate or remarkable improvement whilst no improvement has be noted in the patients who received placebo. The difference was significant ($p=0.035$, $\chi^2$ test). Thus, unlike what the literature seemed to suggest, it has been discovered that nefiracetam has the surprising and unique property of showing a dramatically good activity when given early after stroke. According to the results of this study, the early treatment with nefiracetam after stroke objectively improves the recovery from stroke, as shown by the fact that, beside psychiatric symptoms such as emotional disturbance and reduced spontaneity, also intellectual dysfunction dramatically improved in a high percent of nefiracetam-treated patients whilst no improvement was noted in the placebo-treated patients. Moreover, nefiracetam surprisingly tends to improve neurological signs and incontinence. Thus nefiracetam, when administered early after the event, appears to be the first drug which is able to induce a recovery from stroke or, at least, to improve the recovery from stroke.

The mechanism of action of nefiracetam for this indication, which is not bound to the nootropic activity of the drug, is unknown, but it is believed that its surprising effect in improving ADL of a patient after a stroke or in the recovery of, or at least in improving the recovery of, a post-stroke patient, is due to a true brain repair. This assumption is confirmed by the effect of nefiracetam on spatial learning and retention in rats with cerebral embolism, treated for 9 days with nefiracetam or vehicle, starting within 24 hours of embolization. More particularly, a clear difference between nefiracetam and vehicle-treated animals was observed in the place-learning watermaze task 7 to 9 days after embolization. Moreover, the effect of nefiracetam is maintained even after washout (at day 17 after embolization). This result is predictive of a brain repair effect and shows that the administration of nefiracetam after a stroke provoked by an embolism induces a recovery of the cognition after the stroke.

Thus, it is a second object of the present invention to provide a method for recovering, or at least for improving the recovery of, a post-stroke patient which comprises administering to said patient an effective amount of nefiracetam, said administration being initiated within six months, advantageously within three months, preferably within one month, from the stroke. More particularly, the method comprises the administration to said patients of a pharmaceutical composition containing a pharmacologically effective amount of nefiracetam, as an active ingredient, and a pharmaceutically acceptable carrier. Said effective amount of nefiracetam is advantageously from 50 to 1200 mg, preferably from 100 to 600 mg per unit dose.

It is a third object of the present invention to provide a pharmaceutical composition for the improvement of ADL in post-stroke patients comprising a pharmacologically effective amount of nefiracetam, as an active ingredient, and a pharmaceutically acceptable carrier.

It is a fourth object of the present invention to provide a pharmaceutical composition for the recovery of, or at least for improving the recovery of, a post-stroke patient, comprising a pharmacologically effective amount of nefiracetam, as an active ingredient, and a pharmaceutically acceptable carrier.

It is a fifth object of the present invention to provide the use of nefiracetam for the preparation of a medicament for improving ADL in a post-stroke patient.

It is a sixth object of the present invention to provide the use of nefiracetam for the preparation of a medicament for the recovery, or at least for improving the recovery, of a post-stroke patient.

It is a seventh object of the present invention to provide the use of nefiracetam for the preparation of a medicament for the early treatment of stroke.

It is a eighth object of the present invention to provide a method for treating neurodegeneration in a mammal which comprises administering to said mammal in need of said treatment an effective amount of nefiracetam, more particularly a pharmaceutical composition comprising a pharmacological effective amount of nefiracetam, as an active ingredient, and a pharmaceutically acceptable carrier.

Biological in vitro studies carried out on primary cultures of hippocampal and cortical rat embryo neurons showed that nefiracetam, at concentrations of 0.1, 1, 10 and 100 micromoles/l, displays a neurotrophic effect on said neurons by significantly increasing neurite outgrowth. This effect is similar to that induced by basic Fibroblast Growth Factor (bFGF), for which a function as a neurotrophic factor in the brain has been suggested (R.S. Morrison et al., Proceedings of the National Academy of Sciences, 1986, 83, 7537–7541; K. Abe et al., 1990, 53, 221–227) and such an effect is surprisingly potentiated by bFGF in hippocampal neurons. This finding strongly suggests that nefiracetam, which is well absorbed and crosses the hematoencephalic barrier, should allow the regeneration of damaged brain neurons in mammals, for example after a stroke, thus favoring brain repair and can be used for combating neurodegeneration in mammals, particularly after a stroke.

The oral pharmaceutical compositions in which form nefiracetam will normally be utilized, are prepared in a manner well known per se in the pharmaceutical art and usually comprise nefiracetam, as an active ingredient, in admixture or otherwise in association with a pharmaceutically acceptable carrier or diluent thereof. For making those formulations said active ingredient will usually be mixed with a carrier, or diluted with a diluent, or enclosed or encapsulated in a capsule, sachet, cachet, paper or other suitable container. Suitable carriers and diluents are known per se.

The compositions may be administered to the post-stroke patient for example in the form of tablets, capsules, dragees, suppositories, syrups or suspensions.

The following Example illustrate the invention without, however, limiting it.

EXAMPLE 1

Effect of Nefiracetam on Spatial Learning of Rats with Cerebral Embolism

In male Wistar rats weighing 190–220 g a total of 700 microspheres (48 µm in diameter) were injected into the right common carotid artery of each animal, whereby a quasi-immediate embolism occurs. The embolized animals were randomly divided into 2 groups, each of 13 animals with same neurological deficit, designated as "Control" (embolism plus Vehicle), or "Nefiracetam" (embolism plus nefiracetam 10 mg/kg/day). In addition, a group of 13 "Normal (Sham)" non-embolized animals were used. The administration of nefiracetam or of its vehicle started within the same day of embolization and treatment lasted 9 days. Seven days after embolization, the embolized rats were submitted to a watermaze test, said watermaze being adapted from the Morris water task. The time taken to find the platform (latency) was determined. If a rat failed to find the platform within 180 seconds, the trial was terminated and the rat was assigned a score of 180 seconds. The experiment was carried out in two different sessions. In the first session, at the seventh day embolized rats were submitted to the spatial learning test performed three trials per day for three days (from day 7 to day 9). In the second session, one week after the last day of spatial learning test (i.e., on day 17), a retention test was performed whereby each rat was given three consecutive trials to learn and remember the location of the platform. Table 1 shows the average latency (in seconds) to reach the platform in both spatial learning and retention tests. This table shows the clear difference in learning ability between nefiracetam- and vehicle-treated (control) brain-injured animals when tested at days 7–9 post-embolism. This difference is statistically significant ($p<0.05$ compared to control, t-test). This table also shows a clear effect of nefiracetam in the retention test, wherein a remarkable difference between the nefiracetam- and vehicle-treated, embolized animals is observed.

TABLE 1

| | | Latency (Sec.) | | | |
| --- | --- | --- | --- | --- | --- |
| | | Spatial learning test | | | Retention test |
| Group | n | Day 7 | Day 8 | Day 9 | Day 17 |
| Normal (Sham) | 13 | 130.9 + 16.8 | 61.2 + 15.0 | 22.5 + 5.9 | 31.7 + 13.1 |
| Control | 13 | 159.7 + 11.4 | 146.0 + 13.0 | 127.5 + 17.0 | 133.4 + 15.0 |
| Nefiracetam | 13 | 147.6 + 14.1 | 83.7 + 17.4 | 93.1 + 16.2 | 72.2 + 17.0 |

Table 2 summarizes the number of animals which, under the above-described conditions, failed to find the platform within 180 seconds.

TABLE 2

| | | Number of rats which failed to find the platform within 180 Sec. | | | |
| --- | --- | --- | --- | --- | --- |
| | | Spatial learning test | | | Retention test |
| Group | n | Day 7 | Day 8 | Day 9 | Day 17 |
| Normal (Sham) | 13 | 5 | 1 | 0 | 1 |
| Control | 13 | 10 | 7 | 5 | 7 |
| Nefiracetam | 13 | 8 | 2 | 2 | 2 |

Table 2 shows the clear difference between the nefiracetam-treated animals and the controls.

What is claimed is:

1. A method for aiding cerebral recovery following neurodegeneration in a mammal comprising administering to said mammal in need of said treatment an effective dose of nefiracetam.

2. The method of claim 1 wherein said neurodegeneration is a consequence of a stroke.

3. The method of claim 2 wherein said mammal is a post-stroke human patient.

4. The method of claim 3 wherein said effective dose is administered as a pharmaceutical composition comprising a pharmacologically effective amount of nefiracetam, as an active ingredient, and a pharmaceutically acceptable carrier.

5. The method of claim 4 wherein said composition is in oral unit dose form.

6. The method of claim 5 wherein said administration is made within six months after the stroke.

7. The method of claim 5 wherein said administration is made within three months after the stroke.

8. The method of claim 5 wherein said administration is made within one month after the stroke.

9. The method of claim 5 wherein said effective amount is from 50 to 1200 mg of nefiracetam per unit dose.

10. The method of claim 9 wherein said effective amount is from 100 to 600 mg of nefiracetam per unit dose.

11. The method of claim 6 wherein said effective amount is from 50 to 1200 mg of nefiracetam per unit dose.

12. The method of claim 11 wherein said effective amount is from 100 to 600 mg of nefiracetam per unit dose.

13. The method of claim 7 wherein said effective amount is from 50 to 1200 mg of nefiracetam per unit dose.

14. The method of claim 13 wherein said effective amount is from 100 to 600 mg of nefiracetam per unit dose.

15. The method of claim 8 wherein said effective amount is from 50 to 1200 mg of nefiracetam per unit dose.

16. The method of claim 15 wherein said effective amount is from 100 to 600 mg of nefiracetam per unit dose.

* * * * *